United States Patent
Leigh et al.

(10) Patent No.: US 7,156,815 B2
(45) Date of Patent: Jan. 2, 2007

(54) SOFT TISSUE BIOPSY INSTRUMENT

(75) Inventors: Harold G. Leigh, Iron River, WI (US); Matthew D. Kneen, Minneapolis, MN (US)

(73) Assignee: BioMedical Resources, Inc., Iron River, WI (US)

( * ) Notice: Subject to any disclaimer, the term of this patent is extended or adjusted under 35 U.S.C. 154(b) by 330 days.

(21) Appl. No.: 10/454,270

(22) Filed: Jun. 4, 2003

(65) Prior Publication Data
US 2004/0186393 A1 Sep. 23, 2004

Related U.S. Application Data

(63) Continuation-in-part of application No. 10/391,737, filed on Mar. 19, 2003, now abandoned.

(51) Int. Cl.
A61B 10/00 (2006.01)
A61B 17/32 (2006.01)

(52) U.S. Cl. .................. 600/567; 600/564; 606/172

(58) Field of Classification Search ........ 600/564–568; 604/164.01, 164.12; 607/167, 172
See application file for complete search history.

(56) References Cited

U.S. PATENT DOCUMENTS

| | | | |
|---|---|---|---|
| 3,477,423 A | 11/1969 | Griffith | |
| 4,600,014 A | 7/1986 | Beraha | |
| 4,667,684 A | 5/1987 | Leigh | |
| 4,680,027 A | 7/1987 | Parsons et al. | |
| 4,766,907 A | 8/1988 | de Groot et al. | |
| 4,776,346 A | 10/1988 | Beraha et al. | |
| 4,790,329 A | 12/1988 | Simon | |
| 4,799,495 A | 1/1989 | Hawkins et al. | |
| 4,881,551 A | 11/1989 | Taylor | |
| 4,893,635 A | 1/1990 | de Groot et al. | |
| 4,917,100 A | 4/1990 | Nottke | |
| 4,924,878 A | 5/1990 | Nottke | |
| 4,953,558 A | 9/1990 | Akerfeldt | |
| 4,958,625 A | 9/1990 | Bates et al. | |
| 4,976,269 A | 12/1990 | Mehl | |
| 5,031,634 A | 7/1991 | Simon | |
| 5,036,860 A | 8/1991 | Leigh et al. | |
| 5,056,529 A | 10/1991 | de Groot | |
| RE34,056 E | 9/1992 | Lindgren et al. | |

(Continued)

FOREIGN PATENT DOCUMENTS

EP 1 240 870 A1 9/2002

(Continued)

*Primary Examiner*—Max F. Hindenburg
*Assistant Examiner*—Jonathan Foreman
(74) *Attorney, Agent, or Firm*—Nikolai & Mersereau, P.A.; Thomas J. Nikolai

(57) ABSTRACT

Soft tissue biopsy apparatus for obtaining a tissue specimen comprises a compact handle functioning as a housing having an opening at a front end thereof through which a tubular cannula is arranged to pass. Disposed in the lumen of the cannula is a stylet having a notch formed near its distal end in which a tissue sample is to be captured. First and second springs are operatively coupled individually to the cannula and stylet and a cocking slide incorporating a force reducing mechanism is used to compress the springs while establishing the size of the specimen to be collected in the notch. A trigger mounted on the cocking slide can be used to release the compressed springs in close succession to first advance the end of the stylet beyond the end of the cannula whereby tissue to be extracted flows into the notch and then the spring driving the cannula is released forcing the cannula forward and severing the piece of tissue contained in the notch from surrounding tissue.

12 Claims, 9 Drawing Sheets

U.S. PATENT DOCUMENTS

| | | |
|---|---|---|
| 5,172,701 A | 12/1992 | Leigh |
| 5,172,702 A | 12/1992 | Leigh et al. |
| 5,183,052 A | 2/1993 | Terwilliger |
| 5,183,054 A | 2/1993 | Burkholder et al. |
| 5,195,533 A | 3/1993 | Chin et al. |
| 5,368,045 A | 11/1994 | Clement et al. |
| 5,415,182 A | 5/1995 | Chin et al. |
| 5,526,822 A | 6/1996 | Burbank et al. |
| 5,595,185 A | 1/1997 | Erlich |
| 5,989,196 A | 11/1999 | Chu et al. |
| 6,106,484 A * | 8/2000 | Terwilliger .................. 600/568 |
| 6,120,463 A * | 9/2000 | Bauer ......................... 600/567 |
| 6,273,861 B1 | 8/2001 | Bates et al. |
| 6,358,217 B1 | 3/2002 | Bourassa |

FOREIGN PATENT DOCUMENTS

| | | |
|---|---|---|
| WO | WO 92/03096 | 3/1992 |
| WO | WO 94/03099 | 2/1994 |
| WO | WO 96/04851 | 2/1996 |
| WO | 96/13214 | 5/1996 |

* cited by examiner

SOFT TISSUE BIOPSY INSTRUMENT

CROSS REFERENCE TO RELATED APPLICATION

This application is a continuation-in-part of U.S. patent application Ser. No. 10/391,737, filed Mar. 19, 2003 now abandoned, and entitled "Soft Tissue Biopsy Instrument".

BACKGROUND OF THE INVENTION

1. Field of the Invention

This invention relates generally to a biopsy instrument, and more particularly to an improved apparatus for performing soft tissue biopsy.

2. Discussion of the Prior Art

In the "Background of the Invention" section of U.S. Pat. No. 5,036,860, there is set forth a discussion of prior art soft tissue biopsy devices and the shortcomings of those devices. The contents of U.S. Pat. No. 5,036,860 are hereby incorporated by reference as if set forth in full herein.

The preferred embodiment of the invention described in the '860 patent comprises an elongated housing having somewhat the shape of a ballpoint pin and with a small opening at one end. A first and hollow cannula is positioned within the housing and is reciprocally moveable. One end of the first cannula extends through the opening in the elongate housing and has a sharpened tip for insertion into tissue from which a biopsy specimen is to be taken. A needle-like stylet is positioned within the first cannula and is reciprocally moveable within the lumen of the first cannula. The needle has a sharpened tip for facilitating insertion into tissue and proximate the sharpened tip is a notch or recess into which the tissue specimen projects when the needle is inserted into soft tissue.

The needle stylet is mounted in a slide, allowing it to move independently of the first, outer cannula. A spring and latch mechanism is provided that allows the needle and cannula combination to be placed in a cocked position. Once the device is cocked, it is inserted into the soft tissue from which a specimen is to be withdrawn and the device is "fired". In a two-step sequence, the needle stylet is first returned to its uncocked position and then the outer cannula also is advanced to slide over and sever the biopsy sample from surrounding tissue and to capture the specimen contained in the stylet's notch as the needle and first cannula are simultaneously withdrawn from the target tissue.

During a soft tissue biopsy procedure, it is often desirable to collect multiple samples proximate a suspected tumor or the like. In the prior art devices described in the '860 patent, only a single sample can be taken for any one penetration of tissue by the outer cannula. This is because the outer cannula and the stylet housed therein must be removed from the patient before a first sample can be released for microscopic examination. Thus, it would be advantageous to have a soft tissue biopsy device that would allow multiple samples to be extracted from the patient without having to create multiple puncture wounds, thereby reducing patient trauma.

PCT International Publication WO 96/04851 describes a biopsy instrument that is designed to be fired twice to collect two biopsy specimens in a notched stylet without removing the instrument from the patient's body. However, it has no provision for adjusting the length of the multiple specimens. They are each necessarily of the same length.

While prior art biopsy devices of the type described have permitted adjustment of the sample size to be excised, none, so far as is known, has allowed multiple samples of different sizes to be extracted without having to make multiple punctures with the cannula.

In the prior art arrangement described in the '860 patent, the release of a spring force for driving the sampling stylet results in the triggering of the outer cannula as the stylet reaches its end of travel point. It would be advantageous in an instrument of the type described if the outer cannula movement can be made independent of stylet firing if so desired in a fully automated device.

Then, too, it is important that the soft tissue biopsy instrument provide for one-handed operation and that it be safe to use, having suitable interlocks for preventing premature, unintended firing of the stylet and/or outer cannula.

SUMMARY OF THE INVENTION

The foregoing objects and advantages are achieved by providing a soft tissue biopsy instrument that comprises a housing member having a generally hollow handle that is partitioned into first and second compartments. The housing member has closed distal and proximal ends but with a small aperture formed through the distal end. A tubular cannula of a predetermined inside diameter has a tubular hub affixed to its proximal end. The distal end of the tubular cannula is beveled to a sharp, tissue piercing point and the outside diameter of the cannula allows it to freely pass through the aperture in the distal end of the housing.

The instrument further comprises a stylet that is adapted to be slidably inserted into and removed from the lumen of the cannula. The stylet has a slide member affixed to a proximal thereof and a sharpened distal end. Formed a predetermined distance proximal of the distal end of the stylet is a notch of a predetermined length and depth in which multiple tissue specimens are to be collected. The slide member on the distal end of the stylet is reciprocally moveable in a guideway formed in the housing member. First and second compression springs are individually disposed in the first and second compartments formed in the housing. The first spring is operatively disposed between the housing and the slide member on the proximal end of the stylet and the second spring is operatively disposed between the housing and the tubular hub on the proximal end of the cannula. In order to compress and store energy in the springs, a cocking assembly is slidably mounted on the housing and is operatively coupled to the first and second springs for compressing both springs, while simultaneously retracting the cannula and the stylet in a proximal direction in discrete steps where the number of steps establishes the length of the specimen(s). The cocking assembly further supports a release button which, when depressed, sequentially releases energy stored in the first and second springs to first drive the stylet in the distal direction and then drive the cannula in a distal direction whereby a single tissue sample is cut free of surrounding tissue and retained in the stylet's notch. The device can be recocked to collect a further specimen or the stylet can be withdrawn from the lumen of the cannula without a need to also remove the cannula from its position within the body of the patient. As such, the specimen(s) collected in the stylet's notch can be removed and the stylet replaced within the cannula without having to reinsert the cannula.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
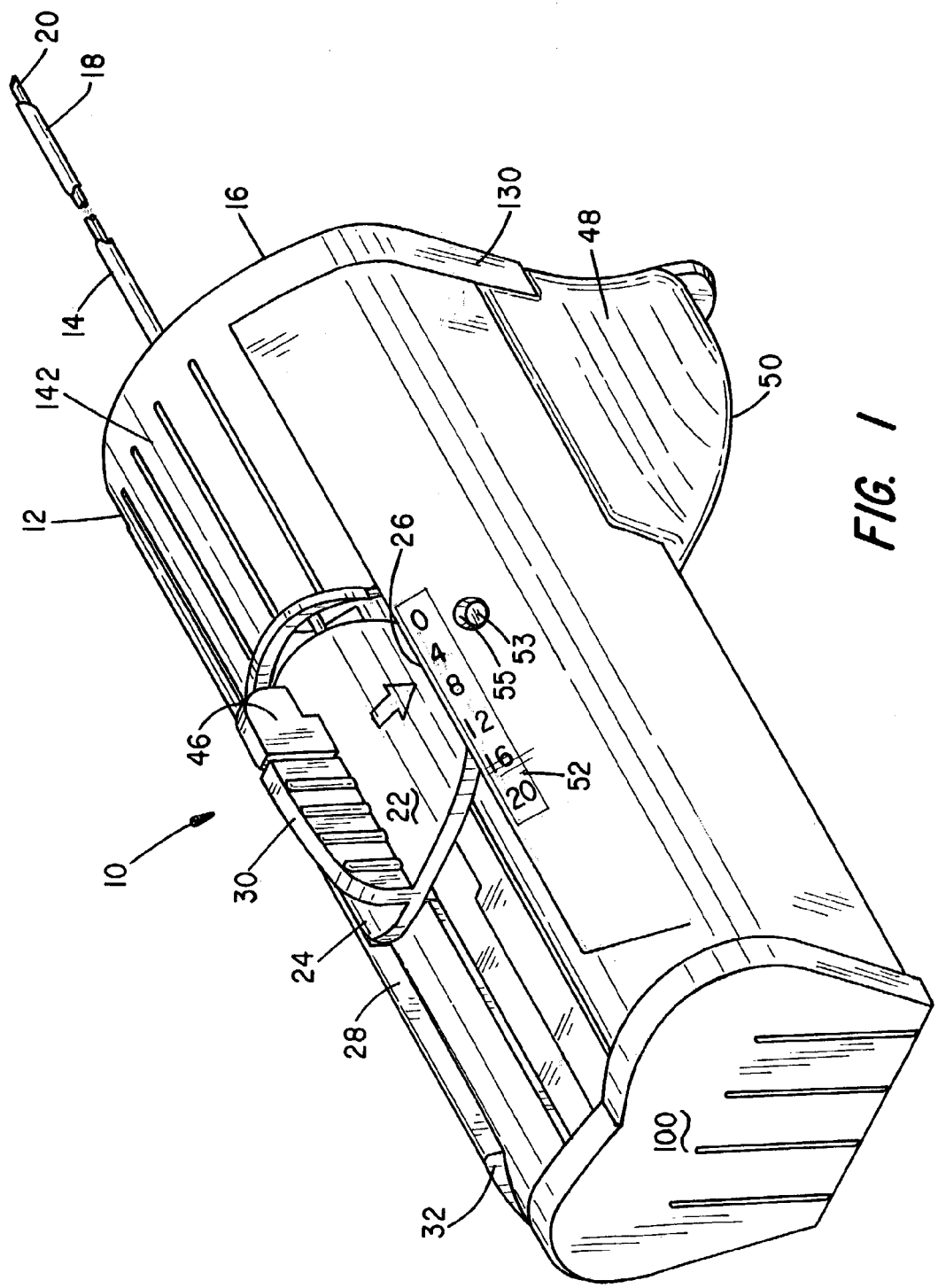
FIG. 1 is a perspective view of the biopsy instrument.

The preferred embodiment of the invention illustrated in the drawings constitutes a new and improved automated tissue biopsy device that permits unique operating features and ease of operation, not available in other commercially available automated needle biopsy devices. Included as features of the invention and described in detail hereinbelow are:

Following insertion of the needle into soft tissue and the firing of the device, a stylet containing the tissue sample can be removed from the device without extracting the biopsy needle from the patient;

The stylet can be replaced in the device and the device can be cocked and refired while it remains in the patient;

Multiple samples of the same or differing length can be collected by multiple cocking and firing sequences without removing the stylet from the cutting cannula.

A single button/slide assembly on the device is used to control all of the functions of the device, namely, the cocking, setting of tissue sample size, sequential or closely simultaneous firing of the stylet and cannula and allows the removal of the stylet from the cannula; a unique firing mechanism built into spring retention sleeves permits automatic firing of both the needle and the cannula either individually or sequentially;

A unique force divider substantially reduces the cocking force, thereby permitting simultaneous cocking of the stylet and cannula drive springs and selective adjustment of the tissue sample size to be extracted. Reduction of the cocking force tends to insure that the cannula will not be moved during the cocking operation;

A unique mechanism prevents the device from being fired before cocking is completed;

A unique sequencing actuator controls the firing sequence whereby the stylet is fired first and the cannula second and also controls the latching sequence whereby needle orientation is properly managed.

The way in which the foregoing features are realized will now be explained. Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Referring to FIG. 1, there is indicated generally by numeral 10 a somewhat enlarged perspective view of a soft tissue biopsy device. It is seen to comprise a molded plastic handle member 12 having an outer needle or cannula 14 projecting through an opening formed in a front face 16 of the device. The needle or cannula 14 is preferably formed from stainless steel and may comprise hypodermic stock of a predetermined length and a diameter in a range of from about 14 ga. to about 20 ga. Its distal end 18 is beveled to a sharp point to facilitate its ability to pass through soft tissue.

The cannula 14 has a lumen for receiving a tissue sampling stylet 20 therethrough. The stylet 20 is affixed to a molded plastic grip member 22 having dove-tail side edges 24 and 26 that ride in a slot 28 provided in the handle 12. The grip member includes an outwardly projecting ear 30 having serrated side surfaces to facilitate its being gripped between a thumb and forefinger to facilitate its being pulled rearward beyond the end 32 of the guideway 28 so that the stylet 20 can be fully extracted from the confines of the outer tubular cannula 14.

Figure 2:
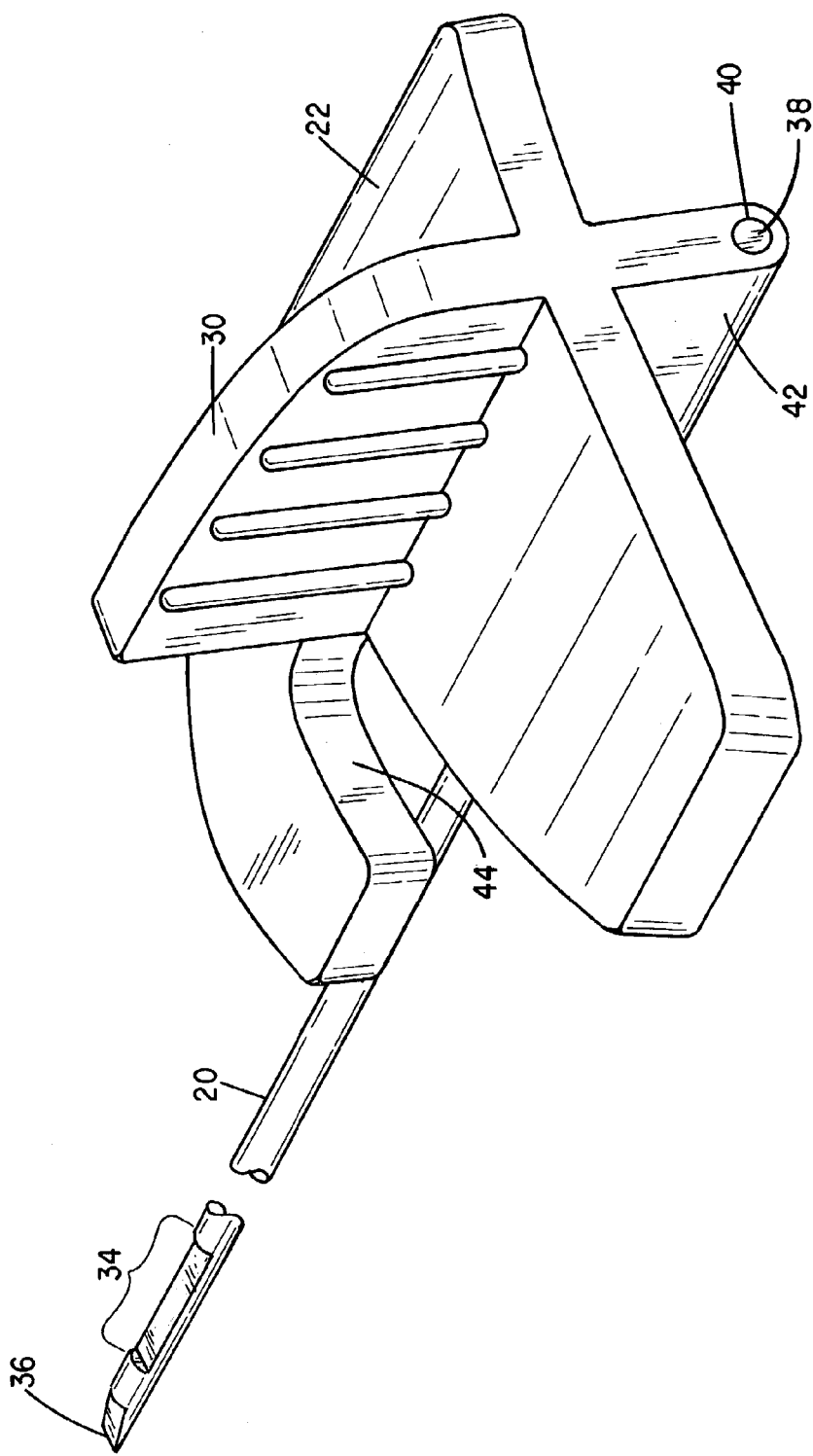
FIG. 2 is a perspective drawing of the stylet used in the biopsy device of FIG. 1.

Referring momentarily to FIG. 2, it will be seen that the stylet 20 includes an elongated notch 34 in which one or multiple sample(s) can be captured and retained following the firing of the device, all as will be further explained. The distal end of the stylet 20 is beveled to a sharp cutting edge 36. Its proximal end 38 extends through a tubular bore 40 formed in a downwardly projecting rib 42 that is integrally formed with the grip member 22. The grip member 22 also includes a transversely extending slot 44 for receiving a latch member 46 (FIG. 1) therein. When the latch member is in the position illustrated in FIG. 1, the grip member 22 is effectively connected to an internal spring-driven ferrule which will be further described when the exploded view of FIG. 4 is explained.

Also slidable mounted to the handle member 12 is a combination cocking slide 48 and firing trigger 50. As the cocking slide 48 is pulled rearward by the user's finger, springs associated with the cannula 14 and stylet 20 are simultaneously compressed to store energy. Also, sliding the cocking lever 48 rearward displaces the grip member 22 rearward to establish how much of the notch 34 will become exposed out the end of the tubular needle 14 during a first phase of the firing sequence of the device. This establishes the size of the specimen that will be collected. To aid the user, a numeric scale 52 is mounted alongside the guideway 28 and a fiducial mark (arrow) on the grip member 22 points to the scale to indicate the size of the sample to be extracted. A further indicator 53 is visible through a hole 55 in the handle 12. When the device has been cocked and is ready to fire, the indicator 53 shows red. Once the trigger 50 has been depressed to fire, both the stylet 20 and the cannula 14, the indicator 53 shows green.

Figure 3:
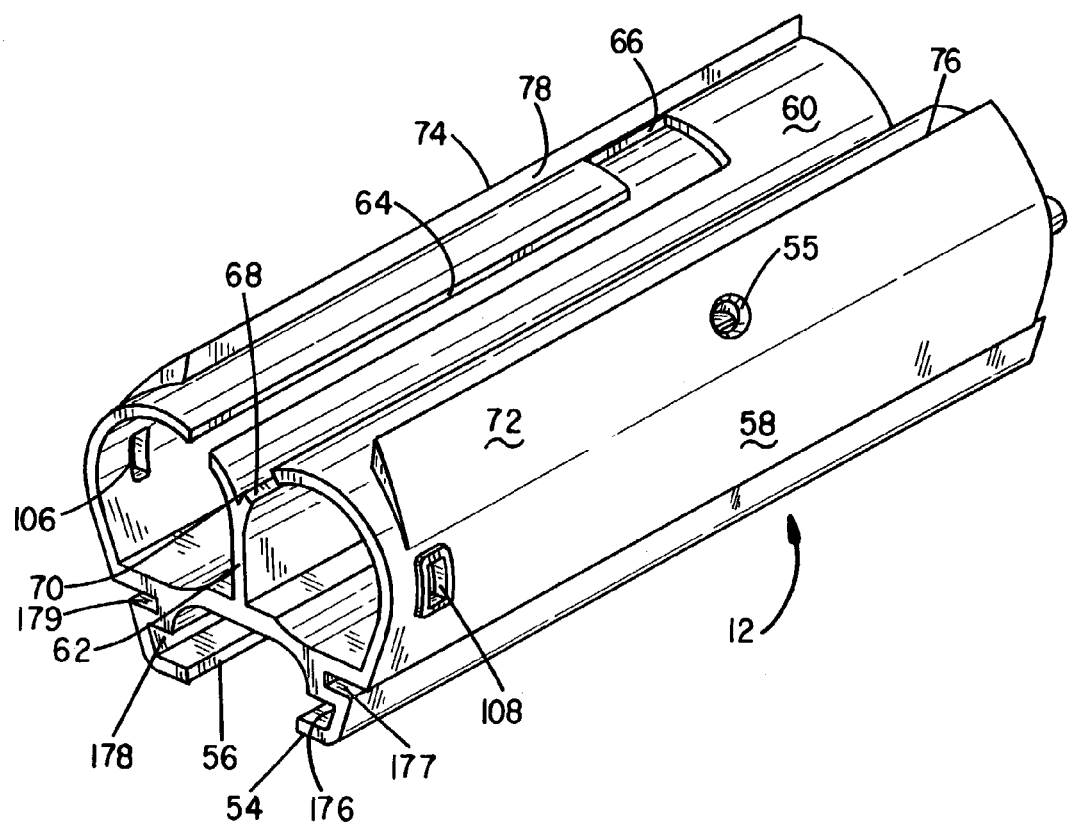
FIG. 3 is a perspective drawing of a piece part comprising the instrument's handle.

A molded piece part comprising the housing 12 is illustrated in perspective in FIG. 3. Molded from a suitable medical grade plastic in an injection molding operation, the housing 12 includes a generally flat base 54 having a slot 56 formed longitudinally through it. Supported on the base are first and second generally tubular portions 58 and 60 with a common wall 62 extending between them. Formed through the thickness dimension of the tubular member 60 is a longitudinally extending slot 64 leading away from a generally rectangular aperture 66. Likewise, the tubular member 58 also includes a longitudinally extending slot 68. The wall 62 where the tubular members 58 and 60 merge with one another define a V-shaped groove 70. Integrally formed with and projecting upwardly from the top surface of the tubular members 58 and 60 are wedge-shaped wings 72 and 74 whose vertical walls 76 and 78 define a guideway for the stylet gripper member 22. That is, the stylet gripper member 22 is dimensioned to fit between the vertical walls 76 and 78 and with the fin 42 resting in the V-shaped groove 70.

Figure 4:
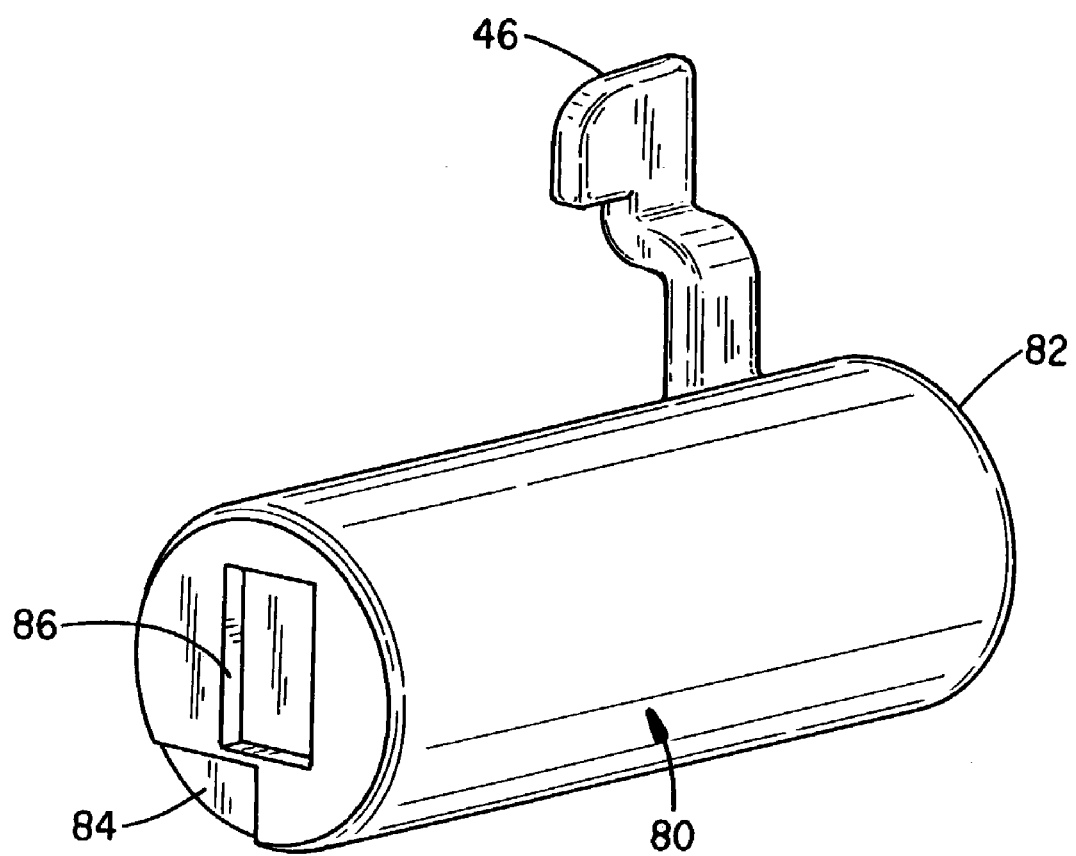
FIG. 4 is a perspective view of the stylet spring retention sleeve.

Referring next to FIG. 4, there is shown a stylet spring retention sleeve 47 which is generally cylindrical and which has the latch member 46 integrally molded therewith. The sleeve 80 has a generally open rearward end 82 and a closed forward end 84. The closed end 84 includes a rectangular aperture 86. The outside diameter of the sleeve 82 is sized so as to allow it to freely slip into the second tubular portion 60 of the handle member 12 with the latch member 46 projecting upward through the slot 64.

Figure 5:
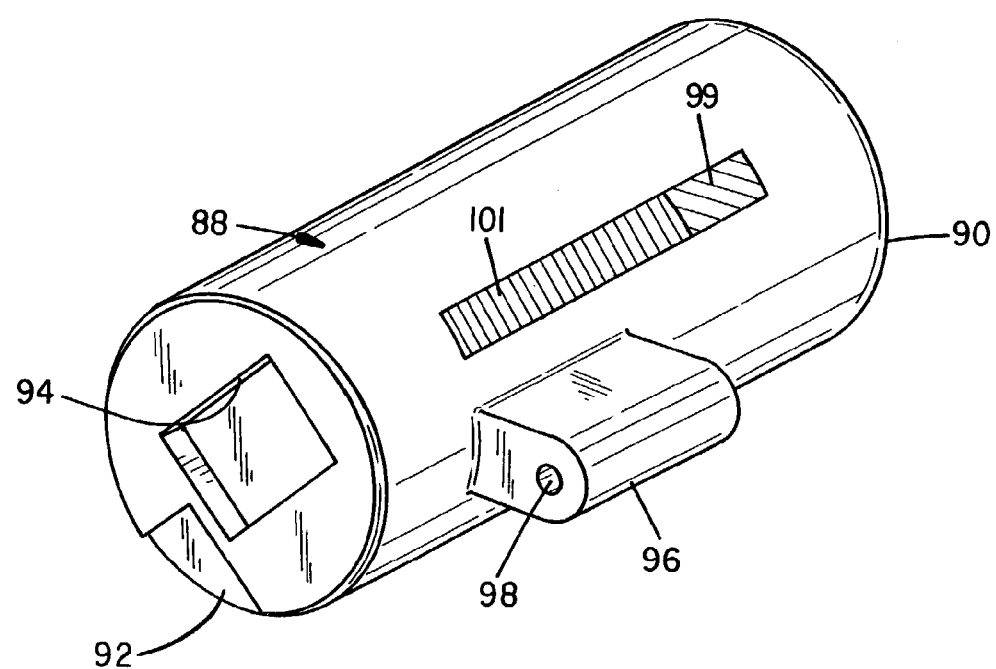
FIG. 5 is a perspective view of the cannula spring retention sleeve.

FIG. 5 is a perspective view of the cannula spring retention sleeve, which is indicated generally by numeral 88. It, too, is cylindrical and hollow with an open rearward end 90 and a closed forward end 92. A rectangular aperture 94 extends through the otherwise closed end 92. Extending radially outward from the exterior surface of the cannula spring retention sleeve 88 is a protuberance 96 that has a bore 98 formed through it for receiving a proximal end portion of the cannula 14 therein. When the sleeve 88 is inserted into the housing member 12, the protuberance 96 extends out through the longitudinal slot 68 when the sleeve 88 is contained within the first tubular portion 58 of the handle 12. Also one or the other of colored areas 99 or 101 will be visible through the aperture 55 depending on whether the device is cocked or not.

Figure 6:
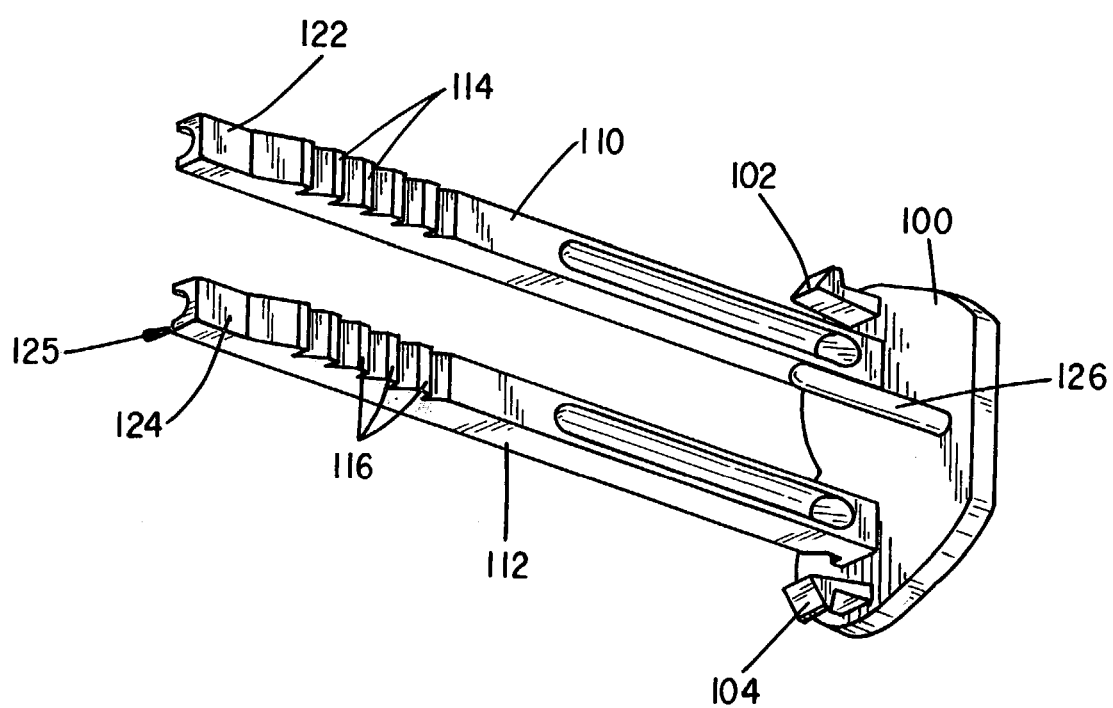
FIG. 6 is a perspective view of the handle's rear cover member.

Turning next to FIG. 6, it shows a perspective view of a rear cover 100 for the housing 12. Projecting outward from the inner face of the cover plate 100 are barb latches 102 and 104 that are adapted to mate with rectangular apertures 106 and 108 formed through the wall of the housing member 12. The barb members 102 and 104 are sufficiently resilient to allow them to deflect as the cover plate 100 is pushed against the rear edge of the housing. Upon reaching the apertures 106 and 108, the barbs spring through those openings to latch the cover in place.

Also projecting perpendicularly from the rear face of the cover plate 100 are longitudinally extending posts 110 and 112 each having a plurality of ratchet teeth 114 and 116 formed thereon. As can be seen in the exploded view of FIG. 10, helically wound compression springs 118 and 120 surround the posts 110 and 112 and fit into the sleeves 80 and 88 that are held within the housing 12 when assembled. The end portions 122 and 124 of the posts 110 and 112 extend through the rectangular openings 86 and 94 formed in the closed ends of the sleeves 80 and 88. The spacing between adjacent ratchet teeth establishes the resolution in specimen size that can be collected.

Referring again to the cover member 100, a further cylindrical post 126 projects perpendicularly from the rear face of the cover 100 and a further compression return spring 128 (FIG. 7) is disposed on the post 126 for a purpose that will be further explained hereinbelow.

Figure 8:
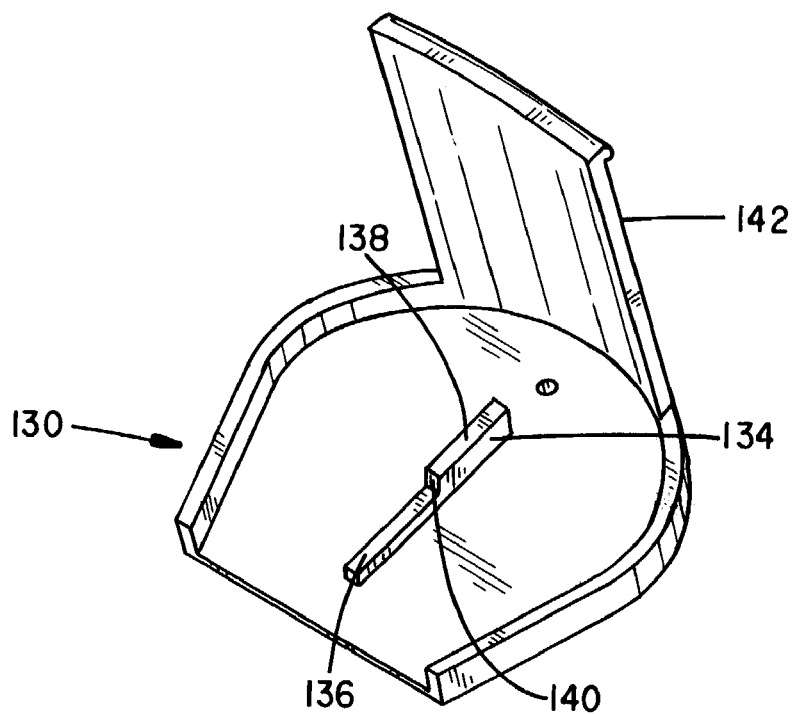
FIG. 8 is a perspective view of the handle's front cover.

The front cover for the housing 12 is shown in FIG. 8 and is indicated generally by numeral 130. A stepped rib 134 having a first portion 136 of a predetermined height dimension and a second portion 138 of approximately twice the height of the portion of the rib 136, thereby defining a stop or shoulder 140 is centrally disposed on the inner surface of the front cover 130 and acts as a glide for a shutter 144.

Integrally molded with the front cover is a top member 142 that fits between the vertical edges 76 and 78 of the wedge-shaped wings 72 and 74 of the handle 12.

Figure 9:
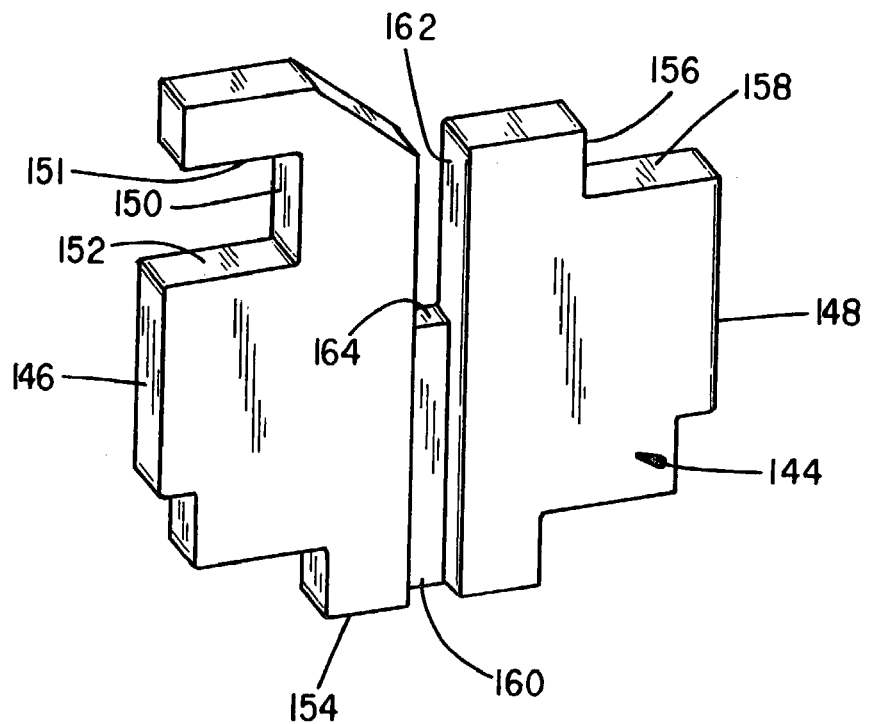
FIG. 9 is a perspective view of the sequence actuating shutter forming part of the assembly of FIG. 1.

FIG. 9 is a perspective view of a sequence actuating shutter 144 which is adapted to cooperate with the stepped rib 134 that is formed on the inner face of the front cover 130. Formed inwardly from the side edge 146 is a notch 150 having a first reference surface 152 at a first predetermined distance from a reference end 154 of the shutter member. In a like way, a notch 156 having a reference surface 158 extends inward from the side edge 148 of the shutter. The reference surface 158 is at a slightly greater displacement from the reference edge 154 than is the reference surface 152. The shutter 144 further includes the central groove 160 formed partially through the thickness dimension of the shutter 144 and leading to a slot 162 that extends completely through the thickness dimension of the shutter. The shutter 144 is juxtaposed to the rear face of the front cover 130 so that the portion 136 of the rib 134 fits within the groove 160 of the shutter while the portion 138 of double thickness extends into the slot 162. The shutter is dimensioned and the groove 160 is sized to allow the shutter 144 to slide relative to the inside surface of the front cover until a point is reached where the shoulder 140 engages the bottom 164 of the slot 162 thereby providing a stop mechanism preventing the posts 110 and 112 from becoming hyper extended. The trigger 50 is likewise protected from over extension.

Figure 10:
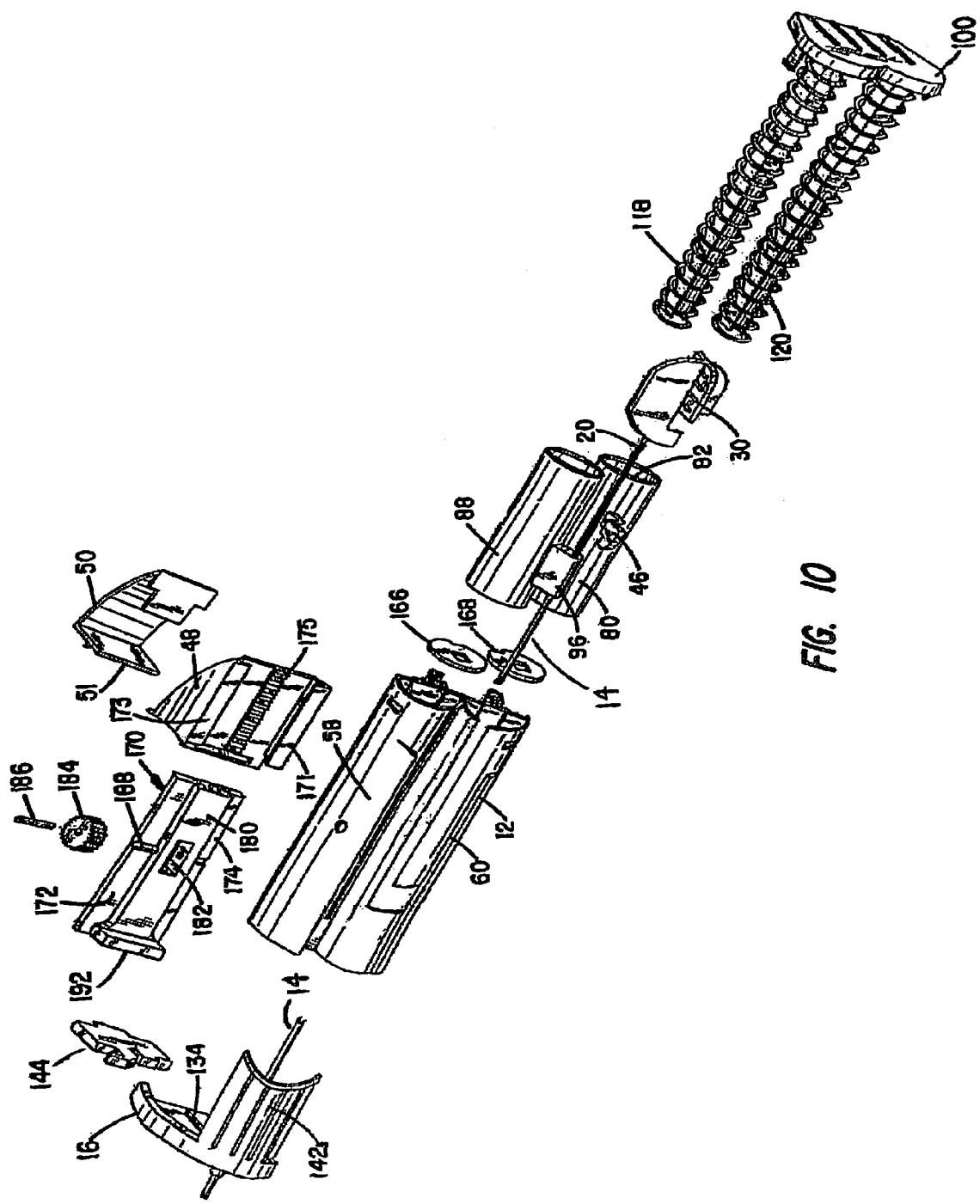
FIG. 10 is an exploded view of the biopsy instrument of FIG. 1 showing the internal components in their appropriate orientation.

Turning now to the exploded assembly drawing of FIG. 10, with the spring retaining sleeves 80 and 88 inserted into the respective first and second tubular portions 58 and 60 (FIG. 3) of the handle 12 and the rear cover plate 100 also affixed to the handle, the inner ends of the springs 118 and 120 abut the closed ends of the sleeves 80 and 88 while the ends 122 and 124 of the posts 110 and 112 extend through the rectangular apertures 86 and 94 of the sleeves. Front cushions 166 and 168 are adhesively affixed to the closed ends of the sleeves 80 and 88 and these cushions or pads have rectangular openings that align with the rectangular openings in the ends of the sleeves 80 and 88.

When the front cover 16 is assembled onto the handle 12, the ends 122 and 124 (FIG. 6) of the posts 110 and 112 fit into the slots 150 and 156 of the sequence actuating shutter 144.

Figure 7:
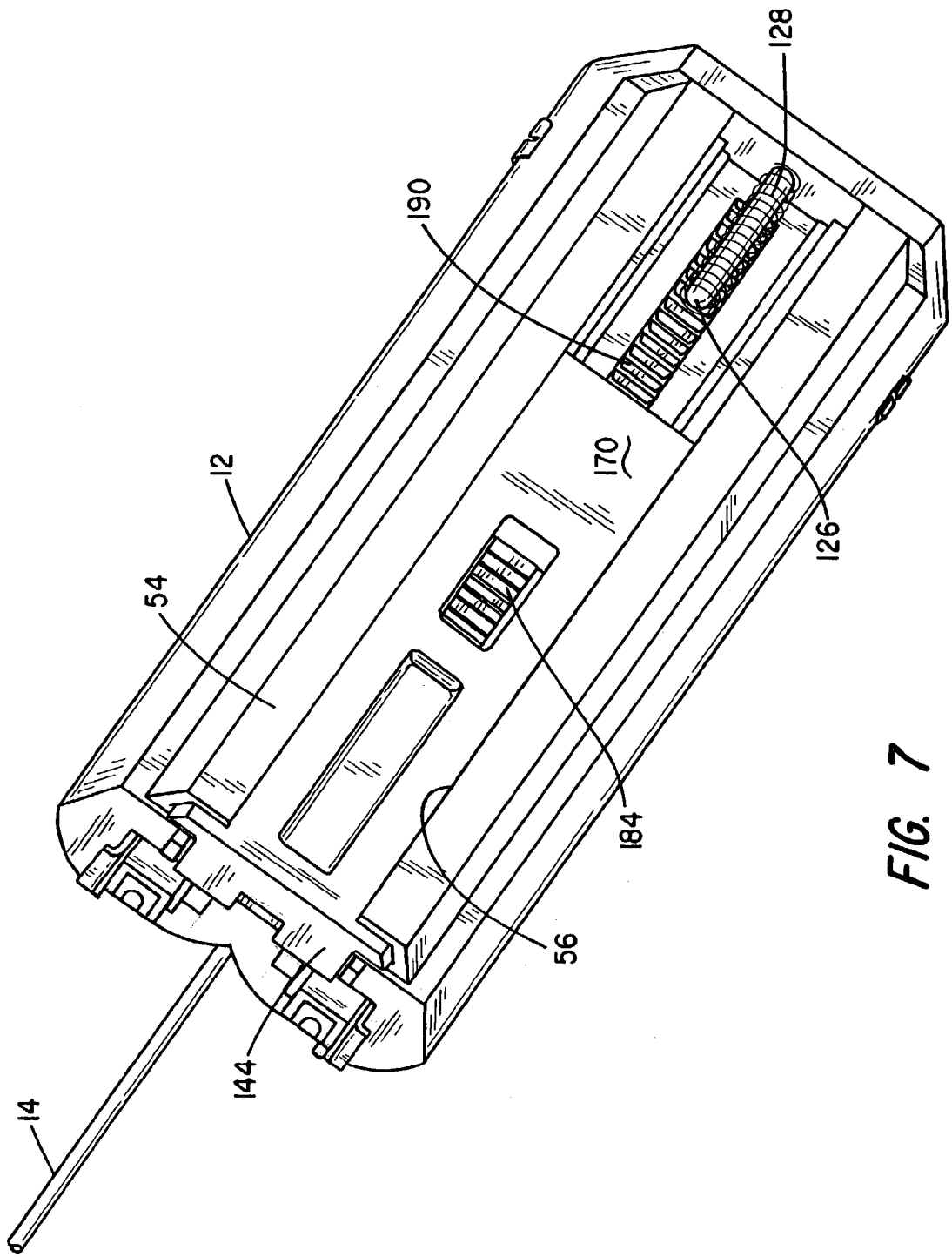
FIG. 7 is a bottom perspective view of the device of FIG. 1 with the cocking and trigger assembly removed.

A slide member 170 (FIG. 10) is dimensioned to fit in sliding relation to the housing 12. More particularly, the slide member 170 includes a pair of flanges 172 and 174 adapted to ride in channels 176 and 178 of the housing 12. The cocking lever 48 has a pair of lateral edge channels 171 and 173 designed to fit into guideways 177 and 179 of housing 12 (FIG. 3). A gear rack 175 is molded into the base of the cocking lever 48. Formed through the raised center portion of the slide plate 170 is a rectangular opening 182 and fitted into that opening is a pinion gear 184 that is journaled for rotation on a pin 186 that passes through a transverse bore 188 formed in the raised center portion 180. With reference to FIG. 7, it can be seen that a similar gear rack 190 is formed along the length of the handle 12 in alignment with the pinion gear 184. The slide 170 further includes an outwardly projecting rib 192 at a front edge thereof that is adapted to cooperate with the closed front ends of the sleeves 80 and 88.

In operation, as the cocking lever 48 is pulled rearward by the user's index finger, the projection 192 on slide 70 is in engagement with the spring retaining sleeves 80 and 88 and pulls those sleeves rearward, compressing the springs 118 and 120 as they move. An edge of the rectangular openings in the spring retention sleeves 80 and 88 engage the teeth 114 and 116 on the posts 110 and 112 to hold the sleeves 80 and 88 in place when finger pressure is removed.

In that the cannula 14 is attached to the protuberance 96 on the sleeve 88 and the stylet moves with the sleeve 80 by virtue of the engagement of the latch member 46 with the transverse slot 44 in the grip member 22, it moves rearward with the displacement of the spring retaining sleeve 80. Once the cocking slide has been drawn rearward a desired measured amount as reflected by the arrow on the stylet grip 22 and the numerical indicia 52, the soft tissue biopsy device is ready for use in collecting a first specimen of a pre-set length.

Using appropriate imaging, the physician advances the cannula 14 and the stylet 20 projecting from the front end 16 of the handle into the area of the body where a tissue sample is to be taken. As the trigger button 50 is depressed, the front edge 51 thereof is brought into engagement with the bottom edge of the sequence actuating shutter 144, displacing it along the guide 136 of the front cover 130 and first elevating the post supporting the spring 120. When that post is elevated to the point where its teeth no longer engage the mating edge of the rectangular aperture 86 of the spring retaining sleeve 80, the spring drives the sleeve 80 forward until its cushioned front end hits the closed end of housing 12. In that the latch member 46 is engaged with the notch 44 of the stylet grip 22, the stylet will be driven into the tissue where the sample is to be taken. The tissue fills the portion of the notch 34 extending beyond the end of the cannula 14. When the release button 50 is further depressed, it elevates the shutter member 144 to the point where the teeth 116 on the post 112 supporting the spring 118 no longer engages the edge of the rectangular opening on the front end of the sleeve 88, thus allowing the spring 118 to drive the sleeve 88 forward against the closed end of the housing 12. This drives the cannula affixed to the protuberance 96 forward to slice the tissue sample contained within the notch of the stylet free of surrounding tissue.

At this point, the cocking lever 48 can again be pulled proximally a desired measured distance while the cannula 18 remains in place within the tissue to again cock the biopsy device in preparation of collecting a further specimen. The distal end of the cannula can be advanced, if desired, and when the trigger 50 is again depressed and the stylet driven distally, the friction between the earlier collected specimen and the inner wall of the cannula will cause the specimen to move to the proximal end of the notch 34, making room for the further specimen to prolapse into the notch before the cannula again is driven distally to sever the specimen from surrounding tissue. This process can be repeated until the notch 34 in the stylet becomes filled.

Now, with the device of the present invention, the tissue sample(s) can be removed from the device without displacing the cannula from its current position within the body. This is done by rotating the latch member 46 out from the notch 44 in the stylet grip 22 and then pulling back on the ear 30 on the grip member to slide the stylet out from the lumen of the cannula 14. Once the tissue sample(s) is removed from the notch in the stylet, the stylet can be replaced by sliding its distal end into the proximal end of the cannula and guiding the grip member 22 to its frontmost position, at which point the latch member 46 can again be rotated into the groove 44, latching the stylet and its grip to the spring retaining sleeve 80. With the instrument still in its position within the body of the patient, it can be recocked by again drawing back on the cocking slide member 48 preparatory to again firing the instrument.

By providing a gear rack on the undersurface of the cocking slide 48 as well as the undersurface of the housing 12, and by providing the pinion gear 184, a mechanical advantage is achieved lessening the finger force required to compress the springs 118 and 120. The arrangement of the pinion gear 184 with the racks reduces the distance traveled by the slide member 170 by a 2:1 ratio, allowing a shorter return spring 128 to be used.

By depressing the firing trigger 50 down firmly in a single stroke, the stylet and the cannula will be advanced in rapid succession determined by the offset in the height of surfaces 158 and 152 relative to the reference surface 154 of the sequence actuating shutter 144. When desired, by slowly depressing the firing trigger 50, the stylet can be advanced without automatically releasing the cannula. By further depressing the firing trigger 50 at a later time, the cannula will be advanced. The surface 151 on shutter 144 (FIG. 9) is arranged to cooperate with the end portion 125 of the post 112 (FIG. 6) to prevent the stylet sleeve 80 from latching until after the cannula sleeve 88 (FIG. 5) becomes latched, thereby synchronizing the latching sequence.

It should be noted that the biopsy device 10 cannot be fired while the cocking action is taking place. Until the cocking lever 48 has been returned to its forwardmost position by the return spring 128, the edge 51 of the trigger button 50 cannot engage the edge 154 of the shutter 144 to lift the posts 110 and 112 so that their teeth no longer engage the bottom edge of the rectangular openings in the two spring retention sleeves.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A soft tissue biopsy instrument comprising:
   (a) a housing member comprising a generally hollow handle partitioned into first and second compartments, the housing member having a closed distal end and a closed proximal end, there being an aperture through the distal end;
   (b) a tubular cannula defining a lumen and having a tubular hub affixed to a proximal end of said cannula and a beveled, tissue piercing distal end, the cannula extending though said aperture;
   (c) a stylet adapted to be slidably inserted and removed from the lumen of the cannula, the stylet having a slide member affixed to a proximal end thereof and a sharpened distal end, the stylet further including a notch of a predetermined length and depth formed proximal of said sharpened distal end, the slide member being reciprocally movable in a guideway formed in the housing member;
   (d) first and second helically wound compression springs individually disposed in said first and second compartments, the first spring operatively disposed between the housing and slide member on the proximal end of the stylet and the second spring operatively disposed between the housing and the tubular hub on the proximal end of the cannula;

(e) a cocking assembly slidably mounted on the housing operatively coupled to the first and second springs for compressing the springs while simultaneously retracting the cannula and the stylet in a proximal direction in a series of discrete steps of a predetermined length without exposing the notch out from the lumen of the tubular cannula;

(f) means coupled to the cocking assembly for reducing a force needed to compress the first and second springs; and (g) a release button for sequentially releasing energy stored in the first and second springs to first drive the stylet in a distal direction and then drive the cannula in a distal direction whereby a tissue specimen of a selectable length is captured in the notch of the stylet.

2. The soft tissue biopsy instrument as in claim 1 and further including a scale on the housing member adjacent a fiducial mark on the slide member for indicating a number of steps by which the cannula and stylet have been retracted in the proximal direction during actuation of the cocking assembly.

3. The soft tissue biopsy instrument as in claim 2 and further including a visual indicator on the first compartment for indicating whether the cocking assembly has been actuated.

4. The soft tissue biopsy instrument as in claim 1 and further including an interlock preventing removal of the stylet from the cannula following actuation of the cocking assembly and prior to activation of the release button.

5. The soft tissue biopsy instrument as in claim 1 wherein the closed proximal end includes first and second ratchet posts projecting longitudinally in the first and second compartments, the ratchet posts passing centrally through the first and second compression springs, said cocking assembly including a pawl for cooperating with the first and second ratchet posts.

6. The soft tissue biopsy instrument as in claim 5 wherein the release button is arranged such that depression thereof disengages the pawl from the first and second ratchet posts in a sequential order.

7. The soft tissue biopsy instrument as in claim 1 wherein said means for reducing the force comprises a slide member slidably affixed to the housing member, a gear rack surface on the cocking assembly, a further gear rack surface on the housing member and a pinion gear journaled for rotation on the first slide member with teeth on the pinion gear engaging the gear rack surface on the cocking assembly and the gear rack surface on the housing member.

8. The soft tissue biopsy instrument as in claim 7 and further including a return spring operatively disposed between the housing member and the slide member.

9. A method for collecting tissue specimens from a target organ in a body of an animal comprising the steps of:

(a) providing a soft tissue biopsy instrument of claim 1;

(b) advancing the tubular cannula into the target organ;

(c) actuating the cocking assembly to simultaneously retract the cannula and stylet in the proximal direction in a series of discrete steps, latching the cocking assembly at a selectable predetermined distance from a terminal location;

(d) actuating the release button to unlatch the cocking assembly and capture the tissue specimen in the notch of the stylet, the specimen length being a function of said selectable predetermined distance;

(e) repeating steps (c) and (d) prior to extracting either the stylet from the tubular cannula or extracting the cannula from the target organ to collect multiple specimens in said notch.

10. The method of claim 9 wherein step (c) is performed prior to step (b).

11. A method for collecting tissue specimens from a target organ in a body of an animal comprising the steps of:

(a) providing a soft tissue biopsy instrument of claim 1;

(b) advancing the tubular cannula into the target organ;

(c) actuating the cocking assembly to retract the cannula and stylet in the proximal direction for a selectable predetermined distance;

(d) actuating the release button to capture the tissue specimen in the notch of the stylet;

(e) removing the stylet from the tubular cannula to extract a collected specimen;

(f) replacing the stylet in the tubular cannula without removing the tubular cannula from the target organ; and (g) repeating steps (c), (d), (e) and (f) to collect multiple specimens from the target organ.

12. The method of claim 11 wherein step (c) is performed prior to step (b).

* * * * *